United States Patent
Sonoke et al.

(10) Patent No.: US 9,872,910 B2
(45) Date of Patent: Jan. 23, 2018

(54) AQUEOUS OPHTHALMIC COMPOSITION

(71) Applicant: FUJIFILM CORPORATION, Minato-ku, Tokyo (JP)

(72) Inventors: Shirou Sonoke, Kanagawa (JP); Yasuyuki Izumi, Kanagawa (JP); Shigetomo Tsujihata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/399,757

(22) Filed: Jan. 6, 2017

(65) Prior Publication Data

US 2017/0112934 A1    Apr. 27, 2017

Related U.S. Application Data

(63) Continuation of application No. PCT/JP2015/069963, filed on Jul. 10, 2015.

(30) Foreign Application Priority Data

Jul. 11, 2014 (JP) .................................. 2014-143641
Mar. 11, 2015 (JP) .................................. 2015-048738

(51) Int. Cl.
| | |
|---|---|
| *A61K 47/32* | (2006.01) |
| *A61K 31/542* | (2006.01) |
| *A61K 47/10* | (2017.01) |
| *A61K 47/12* | (2006.01) |
| *A61K 47/14* | (2017.01) |
| *A61K 9/48* | (2006.01) |
| *A61K 9/10* | (2006.01) |
| *A61K 9/00* | (2006.01) |
| *A61K 47/38* | (2006.01) |

(52) U.S. Cl.
CPC ............ *A61K 47/32* (2013.01); *A61K 9/0048* (2013.01); *A61K 9/10* (2013.01); *A61K 31/542* (2013.01); *A61K 47/38* (2013.01)

(58) Field of Classification Search
CPC ...... A61K 31/542; A61K 47/32; A61K 47/38; A61K 9/08; A61K 9/0048; A61K 47/10; A61K 47/12; A61K 47/183; A61K 47/26; A61K 47/44; A61K 9/10
See application file for complete search history.

(56) References Cited

FOREIGN PATENT DOCUMENTS

| | | |
|---|---|---|
| EP | 582259 A2 | 2/1994 |
| JP | H06-100436 A | 4/1994 |
| JP | H08-295822 A | 11/1996 |
| JP | 2010-37327 A | 2/2010 |
| JP | 2013-512894 A | 4/2013 |
| WO | 2012/053011 A2 | 4/2012 |
| WO | 2013/17528 A1 | 2/2013 |
| WO | 2013/025696 A | 2/2013 |
| WO | WO2013/025696 A1 * | 2/2013 |

OTHER PUBLICATIONS

JPH06100436A translation, original document provided by Applicant in IDS filed Jan. 12, 2017.*
JPH08295622A translation, original document provided by Applicant in IDS filed Jan. 12, 2017.*
Annika Tuomela et al, "Brinzolamide nanocrystal formulations for ophthalmic delivery: Reduction of elevated intraocular pressure in vivo," International Journal of Pharmaceutics, vol. 467, No. 1-2, p. 34-41, Jun. 5, 2014.
International Search Report issued in International Application No. PCT/JP2015/069963 dated Oct. 6, 2015.
Written Opinion of the ISA issued in International Application No. PCT/JP2015/069963 dated Oct. 6, 2015.
Australian Office Action dated Aug. 28, 2017, from the IPA in an Australian patent application No. 2015288644 corresponding to the instant patent application.
English language translation of the following: Office action dated Oct. 10, 2017 from the JPO in a Japanese patent application No. 2016-532990 corresponding to the instant patent application. This office action translation is submitted now in order to supplement the understanding of the reference which is being disclosed in the instant Inforation Disclosure Statement.
New Zealand Office Action dated May 15, 2017, from the New Zealand Patent Office in a New Zealand patent application No. 728131 corresponding to the instant patent application.

* cited by examiner

*Primary Examiner* — Audrea Buckley
(74) *Attorney, Agent, or Firm* — SOLARIS Intellectual Property Group, PLLC

(57) ABSTRACT

An aqueous ophthalmic composition includes a carbonic anhydrase inhibitor; at least one cellulose derivative selected from the group consisting of hydroxypropylmethyl cellulose acetate succinate and carboxymethylethyl cellulose; and water.

7 Claims, No Drawings

AQUEOUS OPHTHALMIC COMPOSITION

CROSS-REFERENCE TO RELATED APPLICATION

This application is a continuation application of International Application No. PCT/JP2015/069963, filed Jul. 10, 2015, the disclosure of which is incorporated herein by reference in its entirety. Further, this application claims priority from Japanese Patent Application No. 2014-143641, filed Jul. 11, 2014, and Japanese Patent Application No. 2015-048738, filed Mar. 11, 2015, the disclosures of which are incorporated herein by reference in their entirety.

BACKGROUND OF THE INVENTION

Field of the Invention

The present invention relates to an aqueous ophthalmic composition.

Description of the Related Art

Carbonic anhydrase inhibitors used in ophthalmic compositions are generally solid and insoluble or hardly soluble in aqueous solvents such as water that are usually used as ophthalmic carriers. Brinzolamide, which is effective as a carbonic anhydrase inhibitor, is also hardly soluble in water. Therefore, at present, carbonic anhydrase inhibitor-containing ophthalmic compositions are used in the form of a suspension. However, in a case in which a carbonic anhydrase inhibitor-containing ophthalmic composition is used in the form of a suspension, it is concerned that, at the time of the administration thereof to the eye, solid particles in the suspension block light and obstruct the field of vision, temporarily causing a phenomenon of blurred vision.

Further, in the use of such an ophthalmic composition in the form of a suspension, it is also concerned that the administration thereof to the eye may cause irritation to the eye if the solid component has a large particle size. Therefore, it is required that solid particles contained in the suspension be fine.

As a method of preparing a suspension including brinzolamide or the like that is effective as a carbonic anhydrase inhibitor, there has been proposed a method of preparing a suspension in which a solution containing brinzolamide and a surfactant is subjected to wet grinding and a thickening agent such as a carboxyvinyl polymer is incorporated into the resulting suspension (see, for example, International Patent Publication No. WO 2012/053011).

Further, Japanese National-Phase Publication (JP-A) No. 2013-512894 discloses a method of preparing a dispersion including carbonic anhydrase inhibitor particles, which method includes: autoclaving a uniformly dispersed slurry containing a carbonic anhydrase inhibitor and a surfactant; sizing the carbonic anhydrase inhibitor particles in the slurry using a microfluidizer; and subsequently mixing the thus processed slurry with a solution that contains water and a polymer such as hypromellose, hydroxyethyl cellulose, hydroxypropyl cellulose, methyl cellulose, or sodium carboxymethyl cellulose.

Moreover, there is proposed a method of producing a brinzolamide dispersion, in which a dispersion is prepared by adding an aqueous solution of a carboxyvinyl polymer to a dispersion including brinzolamide and a surfactant (see, for example, WO 2013/17528).

SUMMARY OF THE INVENTION

In these methods of preparing a carbonic anhydrase inhibitor dispersion that are described in WO2012/053011, JP-A No. 2013-512894, and WO2013/17528, a carbonic anhydrase inhibitor and a surfactant are allowed to coexist for the purpose of improving the dispersibility of the carbonic anhydrase inhibitor. However, in these methods, although a brinzolamide suspension can be obtained, sufficient micronization of particles cannot be achieved even when a surfactant is used, so that blurred vision caused by administration of the suspension to the eye cannot be adequately improved.

An embodiment of the invention relates to an aqueous ophthalmic composition which shows favorable dispersion and stability of fine particles of a carbonic anhydrase inhibitor insoluble or hardly soluble in water.

In the present specification, the term "favorable dispersion" means that particles of a carbonic anhydrase inhibitor are sufficiently micronized. The term "favorable stability" means that, during storage, fine particles of a carbonic anhydrase inhibitor are stably maintained in a dispersed state or, even when precipitation of the fine particles occurred, the particles are maintained in a reversibly precipitated state such that the particles can be redispersed.

The present invention includes the following embodiments.

[1] An aqueous ophthalmic composition including:

a carbonic anhydrase inhibitor; at least one cellulose derivative selected from the group consisting of hydroxypropylmethyl cellulose acetate succinate and carboxymethylethyl cellulose; and water.

[2] The aqueous ophthalmic composition according to [1], in which a content of the carbonic anhydrase inhibitor with respect to the total mass of the aqueous ophthalmic composition is from 0.1% by mass to 10% by mass.

[3] The aqueous ophthalmic composition according to [1] or [2], in which a total content of the cellulose derivative with respect to the total mass of the aqueous ophthalmic composition is from 0.05% by mass to 5% by mass.

[4] The aqueous ophthalmic composition according to any one of [1] to [3], in which the carbonic anhydrase inhibitor is brinzolamide.

[5] The aqueous ophthalmic composition according to any one of [1] to [4], in which the cellulose derivative is hydroxypropylmethyl cellulose acetate succinate.

[6] The aqueous ophthalmic composition according to any one of [1] to [5], further including hydroxypropylmethyl cellulose.

[7] The aqueous ophthalmic composition according to [6], in which a content of the hydroxypropylmethyl cellulose with respect to the total mass of the aqueous ophthalmic composition is from 0.05% by mass to 5% by mass.

[8] The aqueous ophthalmic composition according to any one of [1] to [7], further including a carboxyvinyl polymer.

[9] The aqueous ophthalmic composition according to [8], in which a content of the carboxyvinyl polymer with respect to the total mass of the aqueous ophthalmic composition is from 0.1% by mass to 10% by mass.

According to an embodiment of the present disclosure, there can be provided an aqueous ophthalmic composition which shows favorable dispersion and stability of fine particles of a carbonic anhydrase inhibitor insoluble or hardly soluble in water.

DETAILED DESCRIPTION OF THE INVENTION

Hereinbelow, embodiments of the present disclosure are described.

In the present specification, the term "step" encompasses not only a separate step but also a step which cannot be clearly distinguished from other steps as long as the intended purpose of the step is achieved.

In the present specification, those numerical ranges that are expressed with "to" each denote a range that includes the numerical values stated before and after "to" as the minimum value and the maximum value, respectively.

In the present specification, when reference is made to the amount of a component contained in a composition and there are plural substances corresponding to the same component in the composition, the indicated amount means the total amount of the plural substances present in the composition unless otherwise specified.

The aqueous ophthalmic composition according to an embodiment of the present disclosure is an aqueous ophthalmic composition including: a carbonic anhydrase inhibitor; at least one cellulose derivative selected from the group consisting of hydroxypropylmethyl cellulose acetate succinate and carboxymethylethyl cellulose (hereinafter, may be referred to as "specific cellulose derivative"); and water, and the aqueous ophthalmic composition may further contain other component(s) as required.

The aqueous ophthalmic composition of the present embodiment is an aqueous composition which includes a carbonic anhydrase inhibitor insoluble or hardly soluble in water in the form of particles. In a case in which a cellulose derivative including at least one cellulose derivative selected from the group consisting of hydroxypropylmethyl cellulose acetate succinate and carboxymethylethyl cellulose is incorporated into the aqueous composition, the specific cellulose derivative can efficiently adsorb to the surface of the particle-form carbonic anhydrase inhibitor contained in the aqueous ophthalmic composition.

Since the specific cellulose derivative specifically and stably adsorbs to the fine particles of the carbonic anhydrase inhibitor and the specific cellulose derivative itself is a hydrophilic compound, the fine particles of the carbonic anhydrase inhibitor contained in the aqueous ophthalmic composition have excellent stability and aggregation of the fine particles is thus effectively inhibited.

Accordingly, in the aqueous ophthalmic composition of the present embodiment, the fine particles of the carbonic anhydrase inhibitor are maintained in a stably dispersed state and excellent transparency can be achieved, and this condition is maintained over a long period of time. Therefore, it is believed that the aqueous ophthalmic composition of the present embodiment has favorable storage stability. However, the functions of the cellulose derivative in the aqueous ophthalmic composition are not restricted to those described above.

Aqueous Ophthalmic Composition

Hereinbelow, the components contained in the aqueous ophthalmic composition of the present embodiment are described.

Carbonic Anhydrase Inhibitor

The aqueous ophthalmic composition of the present embodiment includes a carbonic anhydrase inhibitor.

The carbonic anhydrase inhibitor in the aqueous ophthalmic composition of the present embodiment is not particularly restricted as long as it is one which is a solid component insoluble or hardly soluble in water.

Here, the expression "the carbonic anhydrase inhibitor insoluble or hardly soluble in water" means that, when the carbonic anhydrase inhibitor in a free form is dissolved in 25° C. water within a neutral pH range of from 6.0 to 8.0, the solubility of the carbonic anhydrase inhibitor in 1 g (1 mL) of water is 10 mg or less at any pH.

Examples of the carbonic anhydrase inhibitor that can be used in the aqueous ophthalmic composition of the present embodiment include brinzolamide, dorzolamide, acetazolamide, and methazolamide, all of which may be in the form of a salt.

Each of brinzolamide, dorzolamide, acetazolamide, and methazolamide is a carbonic anhydrase inhibitor having a solubility of 10 mg or less in 1 g of 25° C. water at any pH within a neutral range of from 6.0 to 8.0.

In a case in which the carbonic anhydrase inhibitor forms a salt, the salt is not particularly restricted as long as it is a salt that is usually used as a medicine. Examples of the salt include salts with inorganic acids, salts with organic acids, quaternary ammonium salts, salts with halogen ions, salts with alkali metals, salts with alkaline earth metals, metal salts, ammonia salt, and salts with organic amines.

Examples of the salts with inorganic acids include salts with hydrochloric acid, hydrobromic acid, hydroiodic acid, nitric acid, sulfuric acid, or phosphoric acid.

Examples of the salts with organic acids include salts with acetic acid, oxalic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid, or sulfosalicylic acid.

Examples of the quaternary ammonium salts include salts with methyl bromide or methyl iodide.

Examples of the salts with halogen ions include salts with a bromide ion, a chloride ion, or an iodide ion.

Examples of the salts with alkali metals include salts with lithium, sodium, or potassium. Examples of the salts with alkaline earth metals include salts with calcium or magnesium.

Examples of the metal salts include salts with iron or zinc.

Examples of the salts with organic amines include salts with triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, or N,N-bis(phenylmethyl)-1,2-ethanediamine.

The carbonic anhydrase inhibitor contained in the aqueous ophthalmic composition of the present embodiment is preferably at least one selected from the group consisting of brinzolamide and dorzolamide, more preferably brinzolamide.

Brinzolamide can be used in the form of a salt; however, in terms of its use results and of achieving favorable pharmacological effects, brinzolamide is preferably used in a free form that does not constitute a salt.

The aqueous ophthalmic composition of the present embodiment may contain only one carbonic anhydrase inhibitor, or two or more carbonic anhydrase inhibitors.

Here, unless otherwise specified, the content of each component shown below is based on the amount of the component with respect to the amount of the aqueous ophthalmic composition administered to the eye.

In terms of achieving sufficient effect, the content of the carbonic anhydrase inhibitor with respect to the total mass of the aqueous ophthalmic composition is, in terms of the total amount, preferably from 0.1% by mass to 10% by mass, more preferably from 0.2% by mass to 5% by mass, still more preferably from 0.5% by mass to 2% by mass. Here, the content of the carbonic anhydrase inhibitor is the amount in terms of free-form carbonic anhydrase inhibitor.

Specific Cellulose Derivative

The aqueous ophthalmic composition of the present embodiment includes at least one cellulose derivative selected from the group consisting of hydroxypropylmethyl cellulose acetate succinate (hereinafter, may be referred to as "HPMCAS") and carboxymethylethyl cellulose (hereinafter, may be referred to as "CMEC").

The aqueous ophthalmic composition may contain only HPMCAS or CMEC, or a combination of HPMCAS and CMEC, as the specific cellulose derivative.

Particularly, it is preferable that the aqueous ophthalmic composition contains only one of HPMCAS or CMEC. In terms of achieving more favorable dispersion stability, it is more preferable that the aqueous ophthalmic composition contains HPMCAS.

In the aqueous ophthalmic composition of the present embodiment, the total content of the specific cellulose derivative with respect to the carbonic anhydrase inhibitor is in a range of preferably from 0.05 parts by mass to 5 parts by mass, more preferably from 0.1 parts by mass to 3 parts by mass, still more preferably from 0.2 parts by mass to 1.5 parts by mass, in terms of mass ratio with respect to 1 part by mass of the carbonic anhydrase inhibitor.

In a case in which the content ratio of the specific cellulose derivative with respect to 1 part by mass of the carbonic anhydrase inhibitor is in this range, the particles of the carbonic anhydrase inhibitor can be sufficiently micronized and the stability in a dispersed state can be further improved.

In the aqueous ophthalmic composition of the present embodiment, the total content of the specific cellulose derivative is preferably 0.05% by mass to 5% by mass, more preferably 0.1% by mass to 3% by mass, still more preferably 0.2% by mass to 1.5% by mass, with respect to the total mass of the aqueous ophthalmic composition.

In a case in which the content of the specific cellulose derivative with respect to the total mass of the aqueous ophthalmic composition is in this range, the dispersibility and stability of the fine particles of the carbonic anhydrase inhibitor can be further improved.

Hereinbelow, HPMCAS and CMEC, which are specific cellulose derivatives, are described.

HPMCAS

HPMCAS, which is also referred to as "hydroxypropylmethyl cellulose acetate succinate", is a mixed ester composed of acetic acid and monosuccinic acid esters of hydroxymethyl cellulose.

Common HPMCAS is known as a component that contains from 2.0% to 16.0% of acetyl groups ($—COCH_3$: 43.04), from 4.0% to 28.0% of succinyl groups ($—COC_2H_4COOH$: 101.08), from 12.0% to 28.0% of methoxy groups ($—OCH_3$: 31.03) and from 4.0% to 23.0% of hydroxypropoxy groups ($—OC_3H_6OH$: 75.09) by mass, calculated on the dried basis.

Particularly, in terms of inhibiting precipitation of the fine particles of the carbonic anhydrase inhibitor during storage, the HPMCAS used in the aqueous ophthalmic composition of the present embodiment contains acetyl groups at a ratio of preferably from 5% to 14%, more preferably from 5% to 10%, particularly preferably from 5% to 9%, based on mass.

The ratio of succinyl groups contained in the HPMCAS is preferably from 4% to 18%, more preferably from 8% to 18%, particularly preferably from 14% to 18%, based on mass.

The ratio of methoxy groups contained in the HPMCAS is preferably from 20% to 26%, more preferably from 20% to 25%, particularly preferably from 20% to 24%, based on mass.

The ratio of hydroxypropoxy groups contained in the HPMCAS is preferably from 5% to 10%, more preferably from 5% to 9%, based on mass.

The content of these functional groups in the HPMCAS can be quantified by the method described in "the Japanese Pharmacopoeia 16th Edition".

In a case in which the aqueous ophthalmic composition of the present embodiment contains HPMCAS as the specific cellulose derivative, the content thereof is in a range of preferably from 0.05 to 5, more preferably from 0.1 to 3, still more preferably from 0.2 to 1.5, in terms of mass ratio with respect to 1 part by mass of the carbonic anhydrase inhibitor.

By setting the content ratio of HPMCAS with respect to 1 part by mass of the carbonic anhydrase inhibitor in the above-described range, the dispersibility and stability of the fine particles of the carbonic anhydrase inhibitor can be sufficiently improved.

In a case in which the aqueous ophthalmic composition of the present embodiment contains HPMCAS as the specific cellulose derivative, the content thereof is preferably from 0.05% by mass to 5% by mass, more preferably from 0.1% by mass to 3% by mass, still more preferably from 0.2% by mass to 1.5% by mass, with respect to the total mass of the aqueous ophthalmic composition.

By controlling the content of HPMCAS with respect to the total mass of the aqueous ophthalmic composition in the above-described range, the dispersibility and stability of the fine particles of the carbonic anhydrase inhibitor can be sufficiently improved.

CMEC

CMEC is a mixed ether obtained by partial carboxymethylation and ethylation of cellulose as a raw material and is a compound that is also known as an enteric film coating base as listed in "Japanese Pharmaceutical Excipients".

In a case in which the aqueous ophthalmic composition of the present embodiment contains CMEC as the specific cellulose derivative, the content thereof is in a range of preferably from 0.05 to 5, more preferably from 0.1 to 3, still more preferably from 0.2 to 1.5, in terms of mass ratio with respect to 1 part by mass of the carbonic anhydrase inhibitor.

By controlling the content ratio of CMEC with respect to 1 part by mass of the carbonic anhydrase inhibitor in the above-described range, the dispersibility and stability of the fine particles of the carbonic anhydrase inhibitor can be sufficiently improved.

In a case in which the aqueous ophthalmic composition of the present embodiment contains CMEC as the specific cellulose derivative, the content thereof is preferably from 0.05% by mass to 5% by mass, more preferably from 0.1% by mass to 3% by mass, still more preferably from 0.2% by mass to 1.5% by mass, with respect to the total mass of the aqueous ophthalmic composition.

By controlling the content of CMEC with respect to the total mass of the aqueous ophthalmic composition in the above-described range, the dispersibility and stability of the fine particles of the carbonic anhydrase inhibitor can be sufficiently improved.

Other Cellulose Derivative

In the aqueous ophthalmic composition of the present embodiment, a cellulose derivative (hereinafter, may be referred to as "other cellulose derivative") other than the at least one cellulose derivative selected from the group consisting of HPMCAS and CMEC may further be incorporated.

Examples of the other cellulose derivative other than HPMCAS and CMEC include hydroxypropylmethyl cellulose (hereinafter, may be referred to as "HPMC"), hydroxypropyl cellulose, hydroxyethyl cellulose, hydroxyethylmethyl cellulose, methyl cellulose, ethyl cellulose, carboxymethyl cellulose, and hydroxypropylmethyl cellulose phthalate.

The aqueous ophthalmic composition may contain only one other cellulose derivative, or two or more other cellulose derivatives.

HPMC

In terms of further improving the dispersion stability of the carbonic anhydrase inhibitor in the aqueous ophthalmic composition, it is preferable that the aqueous ophthalmic composition contains HPMC as the other cellulose derivative.

The viscosity of HPMC is preferably from 1 mPa·s to 60 mPa·s, more preferably from 1 mPa·s to 30 mPa·s, still more preferably from 1 mPa·s to 7 mPa·s.

In the present specification, the viscosity of HPMC is the viscosity of a 2%-by-mass aqueous solution at 20° C. which is measured by the method described in "the Japanese Pharmacopoeia 16th Edition".

In a case in which the viscosity of HPMC contained in the aqueous ophthalmic composition is in the above-described range, by using HPMC at the time of wet grinding in the production of a dispersion containing the carbonic anhydrase inhibitor, dispersed particles are efficiently formed and finer dispersed particles can thereby be obtained. In addition, in a case in which HPMC is used as a diluent in the preparation of an aqueous ophthalmic composition, the viscosity of the aqueous ophthalmic composition can be adjusted in an appropriate range.

In a case in which the aqueous ophthalmic composition of the present embodiment contains HPMC as the other cellulose derivative, the content thereof is in a range of preferably from 0.05 to 5, more preferably from 0.1 to 3, still more preferably from 0.2 to 1.5, in terms of mass ratio with respect to 1 part by mass of the carbonic anhydrase inhibitor.

By controlling the content ratio of HPMC with respect to 1 part by mass of the carbonic anhydrase inhibitor in this range, the dispersibility and stability of the fine particles of the carbonic anhydrase inhibitor can be further improved.

In a case in which the aqueous ophthalmic composition of the present embodiment contains HPMC as the other cellulose derivative, the content thereof is preferably from 0.05% by mass to 5% by mass, more preferably from 0.1% by mass to 3% by mass, still more preferably from 0.2% by mass to 1.5% by mass, with respect to the total mass of the aqueous ophthalmic composition.

By controlling the content of HPMC with respect to the total mass of the aqueous ophthalmic composition in the above-described range, the dispersibility and stability of the fine particles of the carbonic anhydrase inhibitor can be further improved.

The total amount of the cellulose derivative in the total mass of the aqueous ophthalmic composition of the present embodiment, that is, the total content of the specific cellulose derivative and the other cellulose derivative incorporated as desired, is preferably from 0.1% by mass to 5% by mass, more preferably from 0.2% by mass to 3% by mass, particularly preferably from 0.3% by mass to 1.5% by mass.

By controlling the content of the cellulose derivatives in this range, the dispersibility and stability of the fine particles of the carbonic anhydrase inhibitor can be further improved.

In the aqueous ophthalmic composition of the present embodiment, the total content of the cellulose derivative is in a range of preferably from 0.1 to 5, more preferably from 0.2 to 3, still more preferably from 0.3 to 1.5, in terms of mass ratio with respect to 1 part by mass of the carbonic anhydrase inhibitor.

By controlling the total content of the cellulose derivative with respect to 1 part by mass of the carbonic anhydrase inhibitor in this range, the dispersibility and stability of the fine particles of the carbonic anhydrase inhibitor can be sufficiently improved.

Hereinbelow, components other than the carbonic anhydrase inhibitor and cellulose derivatives, which can be incorporated into the aqueous ophthalmic composition of the present embodiment, are described.

Optional Components in Aqueous Ophthalmic Composition

Sorbic Acid and Salts Thereof

In the aqueous ophthalmic composition of the present embodiment, at least one compound selected from the group consisting of sorbic acid and salts thereof may be incorporated for the purpose of further micronize the particles of the carbonic anhydrase inhibitor.

Examples of the salts of sorbic acid include sodium salt of sorbic acid and potassium salt of sorbic acid and, in terms of its use results as an eye drop, potassium salt of sorbic acid is preferable.

Although sorbates, particularly potassium sorbate, are known as preservatives, it is a novel finding made by the present inventors that the use of a sorbic acid salt in combination with a solid-state carbonic anhydrase inhibitor is useful for micronization of the carbonic anhydrase inhibitor.

In a case in which the at least one compound selected from the group consisting of sorbic acid and salts thereof is used, the content thereof is preferably from 0.01% by mass to 0.1% by mass, more preferably from 0.03% by mass to 0.05% by mass, with respect to the total mass of the aqueous ophthalmic composition.

Carboxyvinyl Polymer

In the aqueous ophthalmic composition of the present embodiment, a carboxyvinyl polymer may be incorporated for the purpose of adjusting the viscosity and improving the stability of the composition.

The carboxyvinyl polymer is preferably one whose 0.5%-by-mass aqueous solution has a viscosity of from 4,000 mPa·s to 40,000 mPa·s at 25° C. and pH 7.5.

In a case in which the aqueous ophthalmic composition contains the carboxyvinyl polymer having a viscosity of the above-described range, the viscosity of the aqueous ophthalmic composition is appropriately maintained, so that favorable retention on the eyeball surface can be provided when the aqueous ophthalmic composition is administered to the eye.

The viscosity of the 0.5%-by-mass aqueous solution of the carboxyvinyl polymer can be measured by the method described in "Japanese Pharmaceutical Excipients 2013".

In a case in which the aqueous ophthalmic composition contains the carboxyvinyl polymer, the content thereof the is preferably from 0.1% by mass to 10% by mass, more preferably from 0.2% by mass to 5% by mass, still more preferably from 0.3% by mass to 1% by mass, with respect to the total mass of the aqueous ophthalmic composition.

In a case in which the content of the carboxyvinyl polymer in the aqueous ophthalmic composition is within this range, the viscosity of the aqueous ophthalmic composition is appropriately maintained, so that favorable retention on the eyeball surface can be provided when the aqueous ophthalmic composition is administered to the eye.

Further, the content of the carboxyvinyl polymer with respect to the carbonic anhydrase inhibitor (carboxyvinyl polymer/carbonic anhydrase inhibitor) is preferably from 0.1 to 10, more preferably from 0.2 to 5, still more preferably from 0.3 to 1, in terms of mass ratio.

By controlling the content ratio of the carboxyvinyl polymer and the carbonic anhydrase inhibitor in the aqueous ophthalmic composition within this range, the viscosity of the aqueous ophthalmic composition can be appropriately maintained, so that favorable retention on the eyeball surface can be provided when the aqueous ophthalmic composition is administered to the eye.

Surfactant

Any known surfactant may be used without particular limitation as long as it is applicable to aqueous ophthalmic compositions, shows favorable biocompatibility without causing irritation, and can improve the dispersion stability of solid particles.

Examples of such a surfactant include anionic surfactants, cationic surfactants, amphoteric surfactants, and non-ionic surfactants, among which non-ionic surfactants are preferable.

Examples of the non-ionic surfactants include alkylaryl polyether alcohol polymers such as tyloxapol; polyoxyethylene-polyoxypropylene polymers (poloxamers) such as PLURONIC (trade name, manufactured by BASF Corp.) or LUTROL (trade name, manufactured by BASF Corp.); polyoxyethylene alkylphenyl ethers such as TRITON X-100 (trade name, manufactured by The Dow Chemical Company); polyoxyethylene fatty acid esters such as polyoxyethylene monostearate (also referred to as "polyoxyl stearate"); polyoxyethylene sorbitan fatty acid esters such as polyoxyethylene sorbitan monooleate, polyoxyethylene sorbitan monolaurate, polyoxyethylene sorbitan monopalmitate, or polyoxyethylene sorbitan monostearate; polyoxyethylene hydrogenated castor oils; sorbitan fatty acid esters such as sorbitan monooleate, sorbitan monolaurate, sorbitan monopalmitate, or sorbitan monostearate; polyoxyethylene castor oils such as polyoxyl 35 castor oil; polyoxyethylene alkyl ethers such as polyoxyethylene lauryl ether; polyoxyethylene fatty acid esters such as polyoxyethylene monostearate; and mixtures thereof.

In a case in which the surfactant is used, the content thereof is preferably from 0.005% by mass to 1.0% by mass, with respect to the total mass of the aqueous ophthalmic composition.

Polyoxyethylene Fatty Acid Ester

The aqueous ophthalmic composition of the present embodiment may include a polyoxyethylene fatty acid ester. In a case in which the polyoxyethylene fatty acid ester is contained, the dispersibility and stability of the fine particles of the carbonic anhydrase inhibitor can be further improved.

Examples of the polyoxyethylene fatty acid ester include polyoxyethylene monostearates (polyoxyl stearates) such as polyoxyl 40 stearate or polyoxyl 55 stearate, among which polyoxyethylene monostearates is preferable in terms of its use results as an eye drop.

The content of the polyoxyethylene fatty acid ester is preferably from 0.001% by mass to 0.1% by mass, more preferably from 0.01% by mass to 0.05% by mass, with respect to the total mass of the aqueous ophthalmic composition.

Isotonizing Agent

The aqueous ophthalmic composition of the present embodiment may include an isotonizing agent.

Examples of the isotonizing agent include those commonly used in eye drops, such as sodium chloride, glycerol, glucose, mannitol, or sorbitol. Among these, sodium chloride is preferable as an isotonizing agent because it shows excellent dispersion when made into a formulation, inhibits the formation of aggregates, and provides a composition having excellent redispersibility. It is preferable that the isotonizing agent is added in such an amount that allows the resulting aqueous ophthalmic composition to have an osmotic pressure equivalent to that of tears, specifically an osmotic pressure ratio (ratio of osmotic pressure with respect to physiological saline) in a range of from 0.9 to 1.2.

Buffer

The aqueous ophthalmic composition of the present embodiment may include a buffer.

Examples of the buffer include acetates such as sodium acetate; phosphates such as sodium dihydrogen phosphate, disodium hydrogen phosphate, potassium dihydrogen phosphate, or dipotassium hydrogen phosphate; ε-aminocaproic acid; amino acid salts such as sodium glutamate; boric acid and salts thereof; and mixtures thereof.

pH-Adjusting Agent

The aqueous ophthalmic composition of the present embodiment may include a pH-adjusting agent.

Examples of the pH-adjusting agent include hydrochloric acid, citric acid, phosphoric acid, acetic acid, tartaric acid, sodium hydroxide, potassium hydroxide, sodium carbonate, and sodium bicarbonate.

The pH of the aqueous ophthalmic composition is adjusted preferably in a range of from 4 to 10 in which irritation to the ocular mucous is generally less, more preferably in a range of from 6 to 8.

Chelating Agent

The aqueous ophthalmic composition of the present embodiment may include a chelating agent.

Examples of the chelating agent include disodium edetate, trisodium edetate, tetrasodium edetate, diethyleneamine pentaacetate, and a mixture thereof. Among these, disodium edetate is preferable.

The content of the chelating agent is preferably from 0.001% by mass to 0.1% by mass, with respect to the total mass of the aqueous ophthalmic composition.

Antioxidant

The aqueous ophthalmic composition of the present embodiment may include an antioxidant.

Examples of the antioxidant include ascorbic acid; an ascorbate such as sodium ascorbate; tocopherol; and a sulfite such as sodium sulfite, potassium sulfite, magnesium sulfite, calcium sulfite, sodium bisulfite, potassium bisulfite, magnesium bisulfite, calcium bisulfite, sodium metabisulfite, potassium metabisulfite, calcium metabisulfite, sodium thiosulfate, or sodium hydrogen sulfite.

Preservative

The aqueous ophthalmic composition of the present embodiment may include a preservative for the purpose of preventing contamination with microorganisms such as fungi or bacteria.

As the preservative, a compound which has antibacterial and antifungal effects, applicable to the eye, and exhibits favorable biocompatibility and suppressed irritation can be selected and used.

Examples of such a preservative include quaternary ammonium salts such as benzalkonium chloride or benzethonium chloride; cationic compounds such as chlorhexidine gluconate; p-hydroxybenzoates such as methyl p-hydroxybenzoate, ethyl p-hydroxybenzoate, propyl p-hydroxybenzoate, or butyl p-hydroxybenzoate; alcohol compounds such as chlorobutanol or benzyl alcohol; sodium dehydroacetate; thiomersal; and mixtures thereof.

Among these, quaternary ammonium salts are preferable because they prevent the aggregate formation of fine particles of the carbonic anhydrase inhibitor and inhibit a reduction in pH, and provide a composition having excellent redispersibility and stability. As such quaternary ammonium salts, benzalkonium chloride and benzethonium chloride are more preferable.

The content of the preservative is preferably in a range of from 0.001% by mass to 0.05% by mass, more preferably in a range of from 0.002% by mass to 0.01% by mass, with respect to the total mass of the aqueous ophthalmic composition.

Other Components

The aqueous ophthalmic composition of the present embodiment may include a polyethylene glycol and the like for the purposes of adjusting the viscosity, improving the stability, and improving the productivity. In terms of its use results as an eye drop, it is preferable to include a polyethylene glycol, and more preferable to include MACROGOL 4000 or MACROGOL 6000.

Method of Producing Aqueous Ophthalmic Composition

The method of producing the aqueous ophthalmic composition of the present embodiment is not particularly restricted, and the aqueous ophthalmic composition of the present embodiment can be produced by applying a known method of producing a suspension or dispersion, such as a dry grinding method, a wet grinding method, or a build-up method.

Among these, in terms of efficiently performing micronization and stabilization of the carbonic anhydrase inhibitor, a wet grinding method is preferably employed. The aqueous ophthalmic composition of the present embodiment is preferably produced by a production method which includes wet grinding a mixture that contains the carbonic anhydrase inhibitor, cellulose derivative(s), water and, as required, other component(s) (this process may be hereinafter referred to as "wet grinding step").

It is preferable that the cellulose derivative contained in the mixture subjected to the wet grinding includes at least one specific cellulose derivative, and it is more preferable that the specific cellulose derivative is HPMCAS. It is still more preferable that the mixture contains HPMCAS and HPMC as the cellulose derivative.

According to this method, since fine particles of the carbonic anhydrase inhibitor obtained by the wet grinding can more efficiently adsorb the specific cellulose derivative, superior dispersibility and stability can be achieved.

Alternatively, a production method in which the carbonic anhydrase inhibitor is wet ground and then the specific cellulose derivative is incorporated into a diluent can be employed.

Since the specific cellulose derivative shows excellent adsorption to fine particles of the carbonic anhydrase inhibitor, the excellent effects of the present embodiment are expressed even when the specific cellulose derivative is added to a dispersion containing fine particles of the carbonic anhydrase inhibitor after the grinding.

Hereinbelow, a preferable method of producing the aqueous ophthalmic composition of the present embodiment is described.

First, after thoroughly stirring an aqueous component(s) such as the specific cellulose derivative and/or the other cellulose derivative with water to dissolve the aqueous component(s) such as the specific cellulose derivative in water, the carbonic anhydrase inhibitor is added to the resulting solution to prepare a mixture, which is subsequently subjected to wet grinding.

The wet grinding can be performed by an ordinary method. The wet grinding can be performed by, for example, using a known wet grinding apparatus such as a ball mill, a bead mill, a roll mill equipped with plural rolls, a colloid mill, or a cone mill. Further, sizing can also be performed using a high-pressure dispersion apparatus or the like, such as the microfluidizer described in JP-A No. 2013-512891.

Particularly, the wet grinding method is preferably a method using a ball mill or a bead mill, more preferably a method using a bead mill, since the carbonic anhydrase inhibitor having very small particle size can be obtained after the wet grinding.

The bead mill may be any of a batch-type apparatus, a circulation-type apparatus, and a continuous-type apparatus, or a combination thereof. The term "batch-type apparatus" refers to an apparatus in which the whole amount of a liquid to be treated is placed and ground in a bead mill container along with a grinding medium. The term "circulation-type apparatus" refers to an apparatus in which a liquid to be treated is allowed to circulate between a tank and a bead mill container. The term "continuous-type apparatus" refers to an apparatus in which a liquid to be treated is allowed to continuously pass through plural bead mill containers.

The diameter of beads used in the bead mill is preferably from 0.03 mm to 5 mm, more preferably from 0.1 mm to 3 mm, still more preferably from 0.3 mm to 1 mm.

In a case in which the beads used in the bead mill is in this range, the resulting dispersion and the beads can be easily separated after the wet grinding, and the carbonic anhydrase inhibitor particles can be efficiently micronized.

Examples of the type of the beads include glass beads, low-alkali glass beads, alkali-free glass beads, zirconia-silica-based ceramic beads, yttria-stabilized zirconia beads, silicon nitride beads, alumina beads, high-purity alumina beads, and titania beads, among which yttria-stabilized zirconia beads are preferable in terms of its use results in the pharmaceutical production.

It is noted here that yttria-stabilized zirconia beads may be simply referred to as "zirconia beads".

In the mixture subjected to wet grinding, in addition to the carbonic anhydrase inhibitor and the water, the specific cellulose derivative, the other cellulose derivative, and/or a variety of optional components can be incorporated as desired.

Further, prior to the treatment of the mixture using a wet grinding apparatus, water can be added to the mixture in an amount required for adjusting the water content suitable for wet grinding. For example, in order to convert the mixture into the form of a slurry suitable for the wet grinding step, water can be added to the mixture in an amount of 5 to 100 times, preferably 5 to 50 times, more preferably 5 to about 25 times the amount of the carbonic anhydrase inhibitor in terms of mass ratio. At the time of the wet grinding, the concentration of the carbonic anhydrase inhibitor is preferably from 0.5 parts by mass to 20 parts by mass, more preferably from 0.8 parts by mass to 12 parts by mass, still more preferably from 1 part by mass to 10 parts by mass, with respect to 100 parts by mass of the mixture to be wet ground.

After connecting a stirring disk to a bead mill apparatus and fitting thereto a bead mill container containing the mixture, the carbonic anhydrase inhibitor that is a solid component is ground into fine particles by performing bead mill dispersion at a rotation speed of preferably from 100 rpm to 10,000 rpm, more preferably from 400 rpm to 6,000 rpm, while cooling the container with a refrigerant, preferably cooling water, at a temperature of preferably from −10° C. to 30° C., more preferably from 2° C. to 15° C.

As a result of performing bead mill dispersion under the above-described conditions, a suspension containing fine particles of the carbonic anhydrase inhibitor can be prepared.

The wet-ground mixture is in the state of a suspension, and this suspension is diluted as required, whereby a suspension having physical properties suitable as an ophthalmic formulation can be prepared.

Dilution Step

If necessary, the thus obtained mixture in the state of a suspension can be diluted with an addition of a diluent containing at least water to produce an ophthalmic formation that has physical properties suitable as an ophthalmic formulation.

The diluent may be a liquid consisting of only water, or a liquid containing an optional component such as a viscosity-adjusting agent or a pH-adjusting agent. By using a diluent containing a viscosity-adjusting agent or the like in accordance with the intended purpose, the suspension can be adjusted to have physical properties suitable as an ophthalmic formulation.

Dilution can be performed by adding, as the diluent, water and other component(s) to be contained as required to the wet-ground mixture, preferably after being sterilized.

Sterilization Step

It is preferable that the resulting aqueous ophthalmic composition is sterilized, taking into consideration the safety in the administration thereof to the eye.

For example, respective components used in the production of an aqueous ophthalmic composition are sterilized, and an aqueous ophthalmic composition can be prepared while maintaining the sterile condition. Sterilization may be performed at the stage before mixing each component to be contained in the resulting aqueous ophthalmic composition, or it may be performed in any of the production steps or after the preparation of the aqueous ophthalmic composition, and sterilization may be performed plural times in a combination of the above-described sterilizations.

Hereinbelow, the sterilization step in the method of producing the aqueous ophthalmic composition of the present embodiment is described.

The carbonic anhydrase inhibitor used in the method of producing the aqueous ophthalmic composition of the present embodiment is a solid component that is a stable compound. The specific cellulose derivative also has excellent thermal stability; therefore, a variety of sterilization processes can be performed on these components.

Examples of the sterilization processes include sterilization by a dry heat treatment; autoclave sterilization by steam, which is one example of moist heat sterilization; filtration sterilization; plasma sterilization; sterilization using a chemical such as a sterilizing agent; sterilization using a sterilizing gas such as ethylene oxide gas; and sterilization by irradiation of radiation such as gamma-ray. In the use of a chemical or a sterilizing gas for sterilization, the effects of residual components and by-products are concerned. Further, in sterilization by irradiation of radiation, generation of an undesirable degradation product is concerned. Therefore, in terms of the reliability, autoclave sterilization, dry heat sterilization, and filtration sterilization are preferable, and autoclave sterilization is more preferable. The mixture subjected to wet grinding is preferably autoclave-sterilized before being wet ground.

Meanwhile, for a component having low thermal stability that is decomposed or deteriorated by heat, it is not preferable to subject such a component to autoclave sterilization. Sterilization of such a component having low thermal stability is not done by heating but by, for example, preferably filtration sterilization or long-term heat sterilization at a low temperature, more preferably filtration sterilization. The filtration sterilization can also be performed on a component having excellent thermal stability.

When filtration sterilization is performed, it is preferable to use a sterilization filter having a pore size of 0.2 μm or less. As the sterilization filter, a commercially available product can be employed.

Absorbance of Aqueous Ophthalmic Composition

The aqueous ophthalmic composition of the present embodiment is a suspension in which carbonic anhydrase inhibitor particles contained therein are fine and reaggregation of the particles is inhibited due to the function of the specific cellulose derivative.

The absorbance of the aqueous ophthalmic composition at a wavelength of 600 nm and an optical path length of 1 mm is preferably 1.1 or less, more preferably 0.7 or less.

In a case in which the absorbance of the aqueous ophthalmic composition of the present embodiment is 1.1 or less, anhydrase inhibitor particles are sufficiently micronized and such fine particles have excellent dispersibility and stability; therefore, the aqueous ophthalmic composition has favorable storage stability. The aqueous ophthalmic composition of the present embodiment also has the advantage that blurred vision after the administration of the composition to the eye can be effectively inhibited.

As described above, the absorbance in the present specification is one which is measured at a wavelength of 600 nm and corresponds to an optical path length of 1 mm. However, for example, in a case in which it is difficult to measure the absorbance at an optical path length of 1 mm due to the physical properties of the aqueous ophthalmic composition such as viscosity, the absorbance may be measured after diluting the aqueous ophthalmic composition with water. When the absorbance of the aqueous ophthalmic composition is measured after dilution with water, the value measured at an optical path length obtained by multiplying 1 mm by the dilution factor is defined as the absorbance at an optical path length of 1 mm. For instance, when the absorbance is measured after 10-fold dilution of the composition, the value is measured at an optical path length of 10 mm. Here, the dilution of the composition is performed at a factor of 1 to 10 in terms of volume ratio. The optical path length is measured at 25° C.

Viscosity of Aqueous Ophthalmic Composition

The viscosity of the aqueous ophthalmic composition obtained by the method of producing an aqueous ophthalmic composition according to the present embodiment is preferably in a range of from 10 mPa·s to 200 mPa·s, more preferably in a range of from 20 mPa·s to 100 mPa·s, at 25° C.

In a case in which the viscosity of the aqueous ophthalmic composition is in this range, it is preferable since the aqueous ophthalmic composition can be comfortably administered to the eye and favorable retention on the eyeball surface can be provided when the aqueous ophthalmic composition is administered to the eye.

The viscosity of the aqueous ophthalmic composition can be measured by the method described in "The Japanese Pharmacopoeia 16th Edition".

In addition to the wet grinding step described above and the dilution step, other step(s) may be performed in the production of the aqueous ophthalmic composition of the present embodiment.

Examples of such an optional step include the above-described sterilization step; a mixing step for preparing the mixture subjected to the wet grinding step; a coarse dispersion step for homogenizing the mixture subjected to the wet grinding step; and steps performed after the wet grinding step and the dilution step, such as a mixing step for further homogenizing the components contained in the resulting suspension or the like, a dispersion step for imparting a shearing force, a pH-adjusting step, a volume-measuring step, and a filling step of filling the resulting aqueous composition into an arbitrary container.

Hereinbelow, the method of producing the aqueous ophthalmic composition of the present embodiment are described more specifically.

In the method of producing the aqueous ophthalmic composition of the present embodiment, for the preparation of the mixture to be wet ground, it is preferable to prepare a liquid that contains autoclavable components, namely the carbonic anhydrase inhibitor, the specific cellulose derivative, and the water, along with, as desired, the optional component having excellent thermal stability such as the other cellulose derivative (hereinafter, this liquid may be referred to as "liquid A") and to subject this liquid to autoclave sterilization.

In a case in which a component having low thermal stability for which autoclave sterilization is not preferable, such as the below-described sorbic acid or the like, is incorporated into the mixture as a component to be wet ground, a liquid that contains the component having low thermal stability and water (hereinafter, this liquid may be referred to as "liquid B") can be prepared separately from the liquid A and subjected to filtration sterilization or the like. The liquid B may contain a component having excellent thermal stability as well, or may be a liquid that contains only sterilized water.

Thereafter, a mixture containing the thus sterilized liquids A and B is prepared, and this mixture can be subjected to the wet grinding step.

Further, in a case in which the dilution step is optionally performed, it is preferable that a diluent used in the dilution step (hereinafter, this liquid may be referred to as "liquid C") is prepared and sterilized in advance.

By wet grinding the above-described mixture that contains the liquids A and B, separating the mixture from the grinding medium, and then diluting the mixture with the liquid C, an aqueous ophthalmic composition having desired physical properties, namely an ophthalmic formulation, can be produced. The grinding medium may be separated from the mixture after diluting the mixture with the liquid C.

The liquid C can be sterilized by a heat sterilization process such as autoclave sterilization.

It is preferable that the specific cellulose derivative is allowed to coexist with the carbonic anhydrase inhibitor when subjected to the wet grinding. However, the specific cellulose derivative can also be incorporated into the aqueous ophthalmic composition by adding the specific cellulose derivative to the liquid C after the wet grinding of the carbonic anhydrase inhibitor. The specific cellulose derivative used in the aqueous ophthalmic composition of the present embodiment is useful for improving the dispersibility and stability of the fine particles of the carbonic anhydrase inhibitor, and the effects of the present embodiment can be exerted even when the specific cellulose derivative is added to the liquid C.

EXAMPLES

The embodiments of the present disclosure are described more specifically below by reference to examples. However, the scope of the present invention is not limited to these examples. Here, "%" and "part(s)" means "% by mass" and "part(s) by mass" unless otherwise specified.

Examples 1 to 10 and Comparative Examples 1 to 6

Each aqueous ophthalmic composition was prepared in accordance with the below-described method.
Preparation of Liquid A
First, an autoclave-sterilizable liquid A that contains a carbonic anhydrase inhibitor was prepared.

Table 1 shows the components and their amounts contained in the liquid A used in the production of the respective aqueous ophthalmic compositions of Examples and Comparative Examples.

Among the components of the liquid A shown in Table 1, raw materials other than brinzolamide as the carbonic anhydrase inhibitor were stirred in a beaker, and in the case of Examples 2 to 9, the pH of the liquid A was adjusted to 7.4 by using sodium hydroxide or hydrochloric acid as a pH-adjusting agent, thereby obtaining a solution in which aqueous components were dissolved.

Brinzolamide, the thus prepared solution, a stirring disk, and 306 g of yttria-stabilized zirconia beads (0.5-mm YTZ balls, manufactured by Nikkato Co., Ltd.) were placed in a bead mill container and stirred, whereby the liquid A was prepared.
Sterilization of Liquid A
A lid was attached to the bead mill container that contains the liquid A, and sterilization was performed using an autoclave (SP200, manufactured by Yamato Scientific Co., Ltd.) at 123° C. for 40 minutes.

TABLE 1

| | Liquid A | | | | | | | (unit g) |
|---|---|---|---|---|---|---|---|---|
| | Brinzolamide | Tyloxapol | HPMC | HPMCAS (AS-HF) | HPMCAS (AS-LF) | Water | pH-adjusting agent | Total amount of liquid A |
| Comparative Example 1 | 4.284 | 0.102 | — | — | — | 29.61 | — | 34 |

TABLE 1-continued

| | Liquid A | | | | | | | |
|---|---|---|---|---|---|---|---|---|
| | Brinzolamide | Tyloxapol | HPMC | HPMCAS (AS-HF) | HPMCAS (AS-LF) | Water | pH-adjusting agent | (unit g) Total amount of liquid A |
| Comparative Example 2 | 4.284 | — | 1.428 | — | — | 28.29 | — | 34 |
| Comparative Example 3 | 4.284 | — | 1.428 | — | — | 28.29 | — | 34 |
| Comparative Example 4 | 4.284 | — | 1.428 | — | — | 28.29 | — | 34 |
| Comparative Example 5 | 4.284 | — | 1.428 | — | — | 28.29 | — | 34 |
| Comparative Example 6 | 4.284 | — | 1.428 | — | — | 28.29 | — | 34 |
| Example 1 | 4.284 | — | 1.428 | — | — | 28.29 | — | 34 |
| Example 2 | 4.284 | — | 1.428 | 1.428 | — | q.s. | q.s. | 34 |
| Example 3 | 4.284 | — | 1.428 | 1.428 | — | q.s. | q.s. | 34 |
| Example 4 | 4.284 | — | 1.428 | — | 1.428 | q.s. | q.s. | 34 |
| Example 5 | 4.284 | — | — | — | 1.428 | q.s. | q.s. | 34 |
| Example 6 | 4.284 | — | 1.428 | — | 1.428 | q.s. | q.s. | 34 |
| Example 7 | 4.284 | — | 1.428 | — | 1.122 | q.s. | q.s. | 34 |
| Example 8 | 4.284 | — | 1.428 | — | 1.122 | q.s. | q.s. | 34 |
| Example 9 | 4.284 | — | 1.428 | — | 1.122 | q.s. | q.s. | 34 |
| Example 10 | 4.284 | — | 1.428 | — | — | 28.29 | — | 34 |

Preparation of Liquid B

Next, a liquid B to be used in a mixture was prepared.

Table 2 shows the components and their amounts contained in the liquid B used in the production of the respective aqueous ophthalmic compositions of Examples and Comparative Examples. As apparent from Table 2, the liquid B was a liquid consisting of only water in some cases.

The components of the liquid B shown in Table 2 were stirred and dissolved in a beaker, and the resultant was then subjected to filtration using a sterilization filter having a pore size of 0.2 μm. In the cases in which water was the sole component of the liquid B, water was directly used.

TABLE 2

| | Polyoxyl 40 stearate | CREMOPHOR ELP | Potassium sorbate | Polyethylene glycol 6000 | (unit g) Water |
|---|---|---|---|---|---|
| Comparative Example 1 | — | — | — | — | 17 |
| Comparative Example 2 | 0.102 | 0.102 | 0.204 | 2.04 | 14.55 |
| Comparative Example 3 | 0.102 | 0.102 | 0.204 | 2.04 | 14.55 |
| Comparative Example 4 | 0.102 | 0.102 | 0.204 | 2.04 | 14.55 |
| Comparative Example 5 | 0.102 | 0.102 | 0.204 | 2.04 | 14.55 |
| Comparative Example 6 | 0.102 | 0.102 | 0.204 | 2.04 | 14.55 |
| Example 1 | 0.102 | 0.102 | 0.204 | 2.04 | 14.55 |
| Example 2 | 0.102 | 0.102 | 0.204 | 2.04 | 14.55 |
| Example 3 | — | — | 0.204 | 2.04 | 14.76 |
| Example 4 | — | — | 0.204 | 2.04 | 14.76 |
| Example 5 | — | — | 0.204 | 2.04 | 14.76 |
| Example 6 | — | — | 0.204 | 2.04 | 14.76 |
| Example 7 | — | — | 0.204 | 2.04 | 14.76 |
| Example 8 | — | — | 0.204 | 2.04 | 14.76 |
| Example 9 | — | — | — | 2.04 | 14.96 |
| Example 10 | — | — | — | 2.04 | 14.96 |

Preparation of Mixture

After the sterilization, the bead mill container that contains the liquid A was taken out of the autoclave and the liquid A was stirred. Then, the liquid B obtained above or water was added to the bead mill container and stirred, whereby a mixture containing at least brinzolamide, a specific cellulose derivative, and water was obtained. In each of Examples 2 to 9, the specific cellulose derivative was contained in the mixture.

Wet Grinding

A stirring disk was connected to a bead mill apparatus (batch-type ready mill; vertical-type bead mill "RMB" manufactured by AIMEX Co., Ltd.) and bead-mill dispersion was performed at a rotation speed of 2,400 rpm for a treatment time of 4.5 hours while cooling the mixture-containing bead mill container with 10° C. cooling water, whereby a dispersion containing pulverized fine particles of brinzolamide as a solid component was obtained.

Preparation of Liquid C

Next, a liquid C used for dilution of the mixture containing fine particles of the carbonic anhydrase inhibitor obtained by the above wet grinding was prepared.

Table 3 shows the components and their amounts contained in the liquid C used in the production of the respective aqueous ophthalmic compositions of Examples and Comparative Examples. As is clear from Tables a and 3, the specific cellulose derivative was contained only in the liquid C in each of Examples 1 to 10, but was contained in both of the liquid A subjected to wet grinding and the liquid C as a diluent.

The components of the liquid C shown in Table 3 were stirred and dissolved in a beaker and the pH of the resultant was adjusted, followed by 20-minute sterilization using an autoclave at 121° C., whereby a liquid C for dilution having a pH of 7.4 was obtained.

TABLE 3

(unit g)

| | MC | CMC-Na | HEC | Sodium alginate | CMEC | HPMCAS (AS-HF) | HPMCAS (AS-LF) | CARBOPOL 971PNF | Disodium edetate | Sodium chloride | MAN-NITOL | pH-adjusting agent (hydrochloric acid, sodium hydroxide) | Water | Total amount of liquid C |
|---|---|---|---|---|---|---|---|---|---|---|---|---|---|---|
| Comparative Example 1 | — | — | — | — | — | — | — | 0.32 | 0.008 | 0.368 | 1.52 | q.s. | q.s. | 70 |
| Comparative Example 2 | — | — | — | — | — | — | — | 0.32 | 0.008 | 0.368 | 1.52 | q.s. | q.s. | 70 |
| Comparative Example 3 | 0.4 | — | — | — | — | — | — | 0.32 | 0.008 | 0.368 | 1.52 | q.s. | q.s. | 70 |
| Comparative Example 4 | — | 0.134 | — | — | — | — | — | 0.32 | 0.008 | 0.368 | 1.52 | q.s. | q.s. | 70 |
| Comparative Example 5 | — | — | 0.134 | — | — | — | — | 0.32 | 0.008 | 0.368 | 1.52 | q.s. | q.s. | 70 |
| Comparative Example 6 | — | — | — | 0.134 | — | — | — | 0.32 | 0.008 | 0.368 | 1.52 | q.s. | q.s. | 70 |
| Example 1 | — | — | — | — | 0.8 | — | — | 0.32 | 0.008 | 0.368 | 1.52 | q.s. | q.s. | 70 |
| Example 2 | — | — | — | — | — | 0.8 | — | 0.32 | 0.008 | 0.368 | 1.52 | q.s. | q.s. | 70 |
| Example 3 | — | — | — | — | — | 0.8 | — | 0.32 | 0.008 | 0.368 | 1.52 | q.s. | q.s. | 70 |
| Example 4 | — | — | — | — | — | — | 0.8 | 0.32 | 0.008 | 0.368 | 1.52 | q.s. | q.s. | 70 |
| Example 5 | — | — | — | — | — | — | 0.4 | 0.32 | 0.008 | 0.368 | 1.52 | q.s. | q.s. | 70 |
| Example 6 | — | — | — | — | — | — | 0.4 | 0.32 | 0.008 | 0.368 | 1.52 | q.s. | q.s. | 70 |
| Example 7 | — | — | — | — | — | — | 0.4 | 0.32 | 0.008 | 0.368 | 1.52 | q.s. | q.s. | 70 |
| Example 8 | — | — | — | — | — | — | — | 0.32 | 0.008 | 0.368 | 1.52 | q.s. | q.s. | 70 |
| Example 9 | — | — | — | — | — | — | — | 0.32 | 0.008 | 0.368 | 1.52 | q.s. | q.s. | 70 |
| Example 10 | — | — | — | — | — | — | 0.8 | 0.32 | 0.008 | 0.368 | 1.52 | q.s. | q.s. | 70 |

Dilution Step

To 70 g of the thus prepared liquid C, 10 g of the mixture (dispersion) containing the liquids A and B prepared in accordance with the amounts of components shown in Tables 1 and 2, which mixture had been subjected to wet grinding, was added, and the resultant was stirred to obtain an aqueous ophthalmic composition containing the respective components in the amounts (% by mass) shown in Tables 4 to 7.

TABLE 4

|  | Comparative Example 1 | Comparative Example 2 | Comparative Example 3 | Comparative Example 4 |
|---|---|---|---|---|
| Component concentration in liquid A (in terms of the concentration in the final aqueous composition, %) | | | | |
| Brinzolamide | 1.05 | 1.05 | 1.05 | 1.05 |
| Tyloxapol | 0.025 | — | — | — |
| HPMC | — | 0.35 | 0.35 | 0.35 |
| HPMCAS (AS-HF) | — | — | — | — |
| HPMCAS (AS-LF) | — | — | — | — |
| Water | q.s. | q.s. | q.s. | q.s. |
| Component concentration in liquid B (in terms of the concentration in the final aqueous composition, %) | | | | |
| Polyoxyl 40 stearate | — | 0.025 | 0.025 | 0.025 |
| CREMOPHOR ELP | — | 0.025 | 0.025 | 0.025 |
| Potassium sorbate | — | 0.05 | 0.05 | 0.05 |
| Polyethylene glycol 6000 | — | 0.5 | 0.5 | 0.5 |
| Water | q.s. | q.s. | q.s. | q.s. |
| Component concentration in liquid C (in terms of the concentration in the final aqueous composition, %) | | | | |
| MC | — | — | 0.5 | — |
| CMC-Na | — | — | — | 0.167 |
| HEC | — | — | — | — |
| Sodium alginate | — | — | — | — |
| CMEC | — | — | — | — |
| HPMCAS (AS-HF) | — | — | — | — |
| HPMCAS (AS-LF) | — | — | — | — |
| Carboxyvinyl polymer (CARBOPOL 971PNF) | 0.4 | 0.4 | 0.4 | 0.4 |
| Disodium edetate | 0.01 | 0.01 | 0.01 | 0.01 |
| Sodium chloride | 0.46 | 0.46 | 0.46 | 0.46 |
| MANNITOL | 1.9 | 1.9 | 1.9 | 1.9 |
| pH-adjusting agent (hydrochloric acid, sodium hydroxide) | q.s. | q.s. | q.s. | q.s. |
| Water | q.s. | q.s. | q.s. | q.s. |
| Post-autoclave pH of liquid C | 7.4 | 7.4 | 7.4 | 7.4 |
| Pre-storage absorbance | 1.453 | 0.257 | 0.237 | 0.133 |
| Evaluation (micronization) | B | A | A | A |
| 40° C. storage period (day) | — | 14 | 14 | 14 |
| Post-storage absorbance | — | 0.875 | 0.881 | 0.877 |
| Change in absorbance (%) | — | 340% | 372% | 659% |
| Change in absorbance based on a 7-day period (%) | — | 220% | 236% | 380% |
| Presence or absence of reversible precipitation | — | absent | absent | absent |
| Evaluation (stability) | — | B | B | B |
| Evaluation (overall) | B | B | B | B |

TABLE 5

|  | Comparative Example 5 | Comparative Example 6 | Example 1 | Example 2 |
|---|---|---|---|---|
| Component concentration in liquid A (in terms of the concentration in the final aqueous composition, %) | | | | |
| Brinzolamide | 1.05 | 1.05 | 1.05 | 1.05 |
| Tyloxapol | — | — | — | — |
| HPMC | 0.35 | 0.35 | 0.35 | 0.35 |
| HPMCAS (AS-HF) | — | — | — | 0.35 |
| HPMCAS (AS-LF) | — | — | — | — |
| Water | q.s. | q.s. | q.s. | q.s. |
| Component concentration in liquid B (in terms of the concentration in the final aqueous composition, %) | | | | |
| Polyoxyl 40 stearate | 0.025 | 0.025 | 0.025 | 0.025 |
| CREMOPHOR ELP | 0.025 | 0.025 | 0.025 | 0.025 |
| Potassium sorbate | 0.05 | 0.05 | 0.05 | 0.05 |
| Polyethylene glycol 6000 | 0.5 | 0.5 | 0.5 | 0.5 |
| Water | q.s. | q.s. | q.s. | q.s. |

TABLE 5-continued

|  | Comparative Example 5 | Comparative Example 6 | Example 1 | Example 2 |
|---|---|---|---|---|
| Component concentration in liquid C (in terms of the concentration in the final aqueous composition, %) | | | | |
| MC | — | — | — | — |
| CMC-Na | — | — | — | — |
| HEC | 0.167 | — | — | — |
| Sodium alginate | — | 0.167 | — | — |
| CMEC | — | — | 1 | — |
| HPMCAS (AS-HF) | — | — | — | 1 |
| HPMCAS (AS-LF) | — | — | — | — |
| Carboxyvinyl polymer (CARBOPOL 971PNF) | 0.4 | 0.4 | 0.4 | 0.4 |
| Disodium edetate | 0.01 | 0.01 | 0.01 | 0.01 |
| Sodium chloride | 0.46 | 0.46 | 0.46 | 0.46 |
| MANNITOL | 1.9 | 1.9 | 1.9 | 1.9 |
| pH-adjusting agent (hydrochloric acid, sodium hydroxide) | q.s. | q.s. | q.s. | q.s. |
| Water | q.s. | q.s. | q.s. | q.s. |
| Post-autoclave pH of liquid C | 7.4 | 7.4 | 7.4 | 7.4 |
| Pre-storage absorbance | 0.135 | 0.155 | 0.926 | 0.349 |
| Evaluation (micronization) | A | A | A | A |
| 40° C. storage period (day) | 14 | 14 | 6 | 11 |
| Post-storage absorbance | 0.826 | 0.889 | 0.988 | 0.35 |
| Change in absorbance (%) | 612% | 574% | 107% | 100% |
| Change in absorbance based on a 7-day period (%) | 356% | 337% | 108% | 100% |
| Presence or absence of reversible precipitation | absent | absent | absent | present |
| Evaluation (stability) | B | B | A | A |
| Evaluation (overall) | B | B | A | A |

TABLE 6

|  | Example 3 | Example 4 | Example 5 | Example 6 |
|---|---|---|---|---|
| Component concentration in liquid A (in terms of the concentration in the final aqueous composition, %) | | | | |
| Brinzolamide | 1.05 | 1.05 | 1.05 | 1.05 |
| Tyloxapol | — | — | — | — |
| HPMC | 0.35 | 0.35 | — | 0.35 |
| HPMCAS (AS-HF) | 0.35 | — | — | — |
| HPMCAS (AS-LF) | — | 0.35 | 0.35 | 0.35 |
| Water | q.s. | q.s. | q.s. | q.s. |
| Component concentration in liquid B (in terms of the concentration in the final aqueous composition, %) | | | | |
| Polyoxyl 40 stearate | — | — | — | — |
| CREMOPHOR ELP | — | — | — | — |
| Potassium sorbate | 0.05 | 0.05 | 0.05 | 0.05 |
| Polyethylene glycol 6000 | 0.5 | 0.5 | 0.5 | 0.5 |
| Water | q.s. | q.s. | q.s. | q.s. |
| Component concentration in liquid C (in terms of the concentration in the final aqueous composition, %) | | | | |
| MC | — | — | — | — |
| CMC-Na | — | — | — | — |
| HEC | — | — | — | — |
| Sodium alginate | — | — | — | — |
| CMEC | — | — | — | — |
| HPMCAS (AS-HF) | 1 | — | — | — |
| HPMCAS (AS-LF) | — | 1 | 0.5 | 0.5 |
| Carboxyvinyl polymer (CARBOPOL 971PNF) | 0.4 | 0.4 | 0.4 | 0.4 |
| Disodium edetate | 0.01 | 0.01 | 0.01 | 0.01 |
| Sodium chloride | 0.46 | 0.46 | 0.46 | 0.46 |
| MANNITOL | 1.9 | 1.9 | 1.9 | 1.9 |
| pH-adjusting agent (hydrochloric acid, sodium hydroxide) | q.s. | q.s. | q.s. | q.s. |
| Water | q.s. | q.s. | q.s. | q.s. |
| Post-autoclave pH of liquid C | 7.4 | 7.4 | 7.4 | 7.4 |
| Pre-storage absorbance | 0.314 | 0.32 | 0.256 | 0.373 |
| Evaluation (micronization) | A | A | A | A |
| 40° C. storage period (day) | 7 | 14 | 14 | 7 |
| Post-storage absorbance | 0.336 | 0.352 | 0.419 | 0.392 |
| Change in absorbance (%) | 107% | 110% | 164% | 105% |

TABLE 6-continued

|  | Example 3 | Example 4 | Example 5 | Example 6 |
|---|---|---|---|---|
| Change in absorbance based on a 7-day period (%) | 107% | 105% | 132% | 105% |
| Presence or absence of reversible precipitation | present | absent | absent | absent |
| Evaluation (stability) | A | A | A | A |
| Evaluation (overall) | A | A | A | A |

TABLE 7

|  | Example 7 | Example 8 | Example 9 | Example 10 |
|---|---|---|---|---|
| Component concentration in liquid A (in terms of the concentration in the final aqueous composition, %) | | | | |
| Brinzolamide | 1.05 | 1.05 | 1.05 | 1.05 |
| Tyloxapol | — | — | — | — |
| HPMC | 0.35 | 0.35 | 0.35 | 0.35 |
| HPMCAS (AS-HF) | — | — | — | — |
| HPMCAS (AS-LF) | 0.275 | 0.275 | 0.275 | — |
| Water | q.s. | q.s. | q.s. | q.s. |
| Component concentration in liquid B (in terms of the concentration in the final aqueous composition, %) | | | | |
| Polyoxyl 40 stearate | — | — | — | — |
| CREMOPHOR ELP | — | — | — | — |
| Potassium sorbate | 0.05 | 0.05 | — | — |
| Polyethylene glycol 6000 | 0.5 | 0.5 | 0.5 | 0.5 |
| Water | q.s. | q.s. | q.s. | q.s. |
| Component concentration in liquid C (in terms of the concentration in the final aqueous composition, %) | | | | |
| MC | — | — | — | — |
| CMC-Na | — | — | — | — |
| HEC | — | — | — | — |
| Sodium alginate | — | — | — | — |
| CMEC | — | — | — | — |
| HPMCAS (AS-HF) | — | — | — | — |
| HPMCAS (AS-LF) | 0.5 | — | — | 1 |
| Carboxyvinyl polymer (CARBOPOL 971PNF) | 0.4 | 0.4 | 0.4 | 0.4 |
| Disodium edetate | 0.01 | 0.01 | 0.01 | 0.01 |
| Sodium chloride | 0.46 | 0.46 | 0.46 | 0.46 |
| MANNITOL | 1.9 | 1.9 | 1.9 | 1.9 |
| pH-adjusting agent (hydrochloric acid, sodium hydroxide) | q.s. | q.s. | q.s. | q.s. |
| Water | q.s. | q.s. | q.s. | q.s. |
| Post-autoclave pH of liquid C | 7.4 | 7.4 | 7.4 | 7.4 |
| Pre-storage absorbance | 0.293 | 0.296 | 0.341 | 0.307 |
| Evaluation (micronization) | A | A | A | A |
| 40° C. storage period (day) | 7 | 7 | 11 | 7 |
| Post-storage absorbance | 0.358 | 0.366 | 0.455 | 0.433 |
| Change in absorbance (%) | 122% | 124% | 133% | 141% |
| Change in absorbance based on a 7-day period (%) | 122% | 124% | 121% | 141% |
| Presence or absence of reversible precipitation | absent | absent | absent | absent |
| Evaluation (stability) | A | A | A | A |
| Evaluation (overall) | A | A | A | A |

The details of the materials shown in Tables 1 to 12 are provided below.

Brinzolamide (carbonic anhydrase inhibitor; manufactured by Indoco Remedies Ltd.)

Tyloxapol (trade name, surfactant manufactured by Sigma-Aldrich Co. LLC.)

HPMCAS (AS-HF) (hydroxypropylmethyl cellulose acetate succinate AS-HF, AQOAT AS-HF, manufactured by Shin-Etsu Chemical Co., Ltd.; specific cellulose derivative)

HPMCAS (AS-LF) (hydroxypropylmethyl cellulose acetate succinate AS-LF, AQOAT AS-LF, manufactured by Shin-Etsu Chemical Co., Ltd.; specific cellulose derivative)

CMEC (carboxymethylethyl cellulose, manufactured by Freund Corp.; specific cellulose derivative)

HPMC (hydroxypropylmethyl cellulose, TC-5E, manufactured by Shin-Etsu Chemical Co., Ltd.; other cellulose derivative)

MC (methyl cellulose, SM-4, manufactured by Shin-Etsu Chemical Co., Ltd.; other cellulose derivative)

CMC-Na (sodium carboxymethyl cellulose, CELLOGEN PR-S, manufactured by DKS Co., Ltd.; other cellulose derivative)

HEC (hydroxyethyl cellulose, manufactured by Tokyo Chemical Industry Co., Ltd.; other cellulose derivative)

Polyoxyl 40 stearate (polyoxyethylene stearate, manufactured by Wako Pure Chemical Industries, Ltd.; polyoxyethylene fatty acid ester)

CREMOPHOR ELP (polyoxyethylene castor oil, manufactured by BASF Corp.)

Potassium sorbate (manufactured by Tokyo Chemical Industry Co., Ltd.)

Polyethylene glycol 6000 (manufactured by Wako Pure Chemical Industries, Ltd.)

Carboxyvinyl polymer (CARBOPOL (registered trademark) 971PNF, manufactured by The Lubrizol Corporation)

Sodium alginate (manufactured by Wako Pure Chemical Industries, Ltd.)

Disodium edetate (manufactured by Wako Pure Chemical Industries, Ltd.)

MANNITOL (MANNIT P, manufactured by Mitsubishi Shoji Foodtech Co., Ltd.)

Water (water for injection, manufactured by Hikari Pharmaceutical Co., Ltd.)

Evaluation of Aqueous Ophthalmic Composition

As indices of the dispersibility and stability of the fine particles of the carbonic anhydrase inhibitor in each aqueous ophthalmic composition and the storage stability of each aqueous composition, the absorbance of the aqueous composition and the rate of change in absorbance were measured.

Measurement of Absorbance

The thus obtained aqueous ophthalmic compositions were each placed in a cell having an optical path length of 1 mm, and the absorbance was measured at a wavelength of 600 nm using a spectrophotometer (NANODROP 1000, manufactured by Thermo Fisher Scientific Inc). The measurement was performed at 25° C. The results thereof are shown in Tables 4 to 7. It was judged that the brinzolamide particles were sufficiently micronized when the absorbance was 1.1 or lower. The evaluation criteria were as follows.

A: The absorbance was 1.1 or lower (sufficient micronization of the particles).

B: The absorbance was higher than 1.1 (insufficient micronization of the particles).

Storage Stability

1. Change in Absorbance

The thus obtained aqueous ophthalmic compositions were each stored at a temperature of 40° C. for the respective periods shown in Tables 4 to 7, and the absorbance of each aqueous ophthalmic composition after the storage was measured under the same conditions as described above. The results thereof are shown in Tables 4 to 7.

The post-storage absorbance and the change in absorbance, which was calculated from the pre-storage absorbance and the post-storage absorbance, are shown in Tables 4 to 7. In addition, the change in absorbance based on a storage period of 7 days was calculated using the following equation, and the results thereof are also shown in Tables 4 to 7.

(Change in absorbance based on a 7-day period)=
100+[(Post-storage absorbance)−(Pre-storage absorbance)]÷(Pre-storage absorbance)×7÷[40° C. storage period (day)]×100

The stability was evaluated as excellent when the change in absorbance based on a 7-day period was 150% or lower. The evaluation criteria were as follows.

A: The change in absorbance based on a 7-day period was 150% or less (sufficient stability).

B: The change in absorbance based on a 7-day period was higher than 150% (insufficient stability).

2. Presence or Absence of Reversible Precipitation

The thus obtained aqueous ophthalmic compositions were each stored at a temperature of 40° C. for the respective periods shown in Tables 4 to 7, and the presence or absence of precipitation of particles in each aqueous ophthalmic composition after the storage was visually observed. The results thereof are shown in Tables 4 to 7.

Precipitation was observed in Examples 2 and 3; however, it was reversible precipitation that was easily redispersed by application of vibration thereto, and the level of the precipitation presented no practical problem.

As shown in Tables 4 to 7, it is understood that the aqueous ophthalmic compositions of Examples all showed favorable dispersibility and stability of the fine particles of the carbonic anhydrase inhibitor and had excellent storage stability. Moreover, these aqueous ophthalmic compositions had both a post-preparation absorbance and a post-storage absorbance of 1.1 or lower, a level at which blurred vision caused by administration of each composition to the eye can be inhibited.

From the results of Example 10, it is understood that the effects of the present embodiment can be exerted even when the specific cellulose derivative is not added at the time of the wet grinding but at the time of the dilution. Further, from a comparison between Examples 1 and 4, it is understood that, as compared to a case in which CMEC was used as a diluent, the use of HPMCAS as a diluent resulted in a lower pre-storage absorbance, a lower post-storage absorbance, and a lower change in absorbance, which indicates superior dispersibility and stability of the fine particles.

Examples 11 to 14

Each aqueous ophthalmic composition was prepared in accordance with the below-described method.

Preparation of Liquid A

First, an autoclave-sterilizable liquid A that contains a carbonic anhydrase inhibitor was prepared.

Table 8 shows the components and their amounts contained in the liquid A used in the production of the respective aqueous ophthalmic compositions of Examples.

Among the components of the liquid A shown in Table 8, raw materials other than brinzolamide as the carbonic anhydrase inhibitor were stirred in a beaker, and the pH of the liquid A was adjusted to 7.4 by using sodium hydroxide or hydrochloric acid as a pH-adjusting agent, thereby obtaining a solution in which aqueous components were dissolved.

Brinzolamide, the thus prepared solution, a stirring disk, and 306 g of yttria-stabilized zirconia beads (0.5-mm YTZ balls, manufactured by Nikkato Co., Ltd.) were placed in a bead mill container and stirred, whereby the liquid A was prepared.

Moist Heat Sterilization of Liquid A

A lid was attached to the bead mill container that contains the liquid A, and moist heat sterilization was performed using an autoclave (SP200, manufactured by Yamato Scientific Co., Ltd.) at 123° C. for 40 minutes.

TABLE 8

| | Liquid A | | | (unit g) |
|---|---|---|---|---|
| | Example 11 | Example 12 | Example 13 | Example 14 |
| Brinzolamide | 4.284 | 3.213 | 2.142 | 1.607 |
| HPMC | 0.816 | 0.612 | 0.408 | 0.306 |
| HPMCAS (AS-LF) | 1.122 | 0.842 | 0.561 | 0.421 |
| pH-adjusting agent | q.s. | q.s. | q.s. | q.s. |
| Water | q.s. | q.s. | q.s. | q.s. |
| Total amount of liquid A | 34 | 25.5 | 17 | 12.5 |

Preparation of Liquid B

Next, a liquid B to be used in a mixture was prepared.

Table 9 shows the components and their amounts contained in the liquid B used in the production of the respective aqueous ophthalmic compositions of Examples 11 to 14.

The components of the liquid B shown in Table 9 were stirred and dissolved in a beaker, and the resultant was then subjected to filter sterilization using a sterilization filter having a pore size of 0.2 μm.

TABLE 9

| Liquid B | |
| --- | --- |
| | (unit g) |
| | Examples 11 to 14 |
| Polyethylene glycol 6000 | 6 |
| Water | 44 |

Preparation of Liquid C

Next, a liquid C was prepared.

Table 10 shows the components and their amounts contained in the liquid C used in the production of the respective aqueous ophthalmic compositions of Examples. The liquid C of the same composition was used in each of Examples 11 to 14. However, as described below, the order of adding the liquid C was different between Examples.

The components of the liquid C shown in Table 10 were stirred and dissolved in a beaker and the pH of the resultant was adjusted, followed by 20-minute moist heat sterilization using an autoclave at 121° C., whereby a liquid C for dilution having a pH of 7.4 was obtained.

TABLE 10

| Liquid C | |
| --- | --- |
| | (unit g) |
| | Examples 11 to 14 |
| Carboxyvinyl polymer (CARBOPOL 971PNF) | 0.64 |
| Disodium edetate | 0.016 |
| Sodium chloride | 0.736 |
| MANNITOL | 3.04 |
| pH-adjusting agent (hydrochloric acid, sodium hydroxide) | q.s. |
| Water | q.s. |
| Total amount of liquid C | 140 |

Preparation of Mixture

After the sterilization, the bead mill container that contains the liquid A was taken out of the autoclave and the liquid A was stirred. Then, a liquid selected from the liquids B and C obtained above and water was added to the bead mill container in the amounts shown below.

Example 11

The Liquid B was added in an amount of 17 g.

Example 12

The liquids B and C were added in amounts of 12.75 g and 12.75 g, respectively.

Example 13

The liquid B and water were added in amounts of 8.5 g and 25.5 g, respectively.

Example 14

The liquid B and water were added in amounts of 6.375 g and 31.875 g, respectively.

After adding the above-described liquid, the resultant was further stirred to obtain each mixture to be wet ground in Examples 11 to 14. The compositions of the mixtures to be wet ground in these Examples are shown in Table 11 below.

TABLE 11

| Mixture | | | | |
| --- | --- | --- | --- | --- |
| | | | | (unit g) |
| | Example 11 | Example 12 | Example 13 | Example 14 |
| Brinzolamide | 4.284 | 3.213 | 2.142 | 1.607 |
| HPMC | 0.816 | 0.612 | 0.408 | 0.306 |
| HPMCAS (AS-LF) | 1.122 | 0.842 | 0.561 | 0.421 |
| Polyethylene glycol 6000 | 2.04 | 1.53 | 1.02 | 0.765 |
| Carboxyvinyl polymer (CARBOPOL 971PNF) | — | 0.0583 | 0.117 | 0.146 |

TABLE 11-continued

| | Mixture | | | |
|---|---|---|---|---|
| | | | | (unit g) |
| | Example 11 | Example 12 | Example 13 | Example 14 |
| Disodium edetate | — | 0.0015 | 0.0029 | 0.0036 |
| Sodium chloride | — | 0.067 | 0.134 | 0.168 |
| MANNITOL | — | 0.277 | 0.554 | 0.692 |
| pH-adjusting agent (hydrochloric acid, sodium hydroxide) | q.s. | q.s. | q.s. | q.s. |
| Water | q.s. | q.s. | q.s. | q.s. |
| Total amount of mixture | 51 | 51 | 51 | 51 |
| Time required for wet grinding | 18 hr | 3.5 hr | 2 hr | 1.5 hr |

Wet Grinding

A stirring disk was connected to a bead mill apparatus (batch-type ready mill; vertical-type bead mill "RMB" manufactured by AIMEX Co., Ltd.) and bead-mill dispersion was performed at a rotation speed of 800 rpm while cooling the mixture-containing bead mill container with 10° C. cooling water, and 1 g of the thus obtained dispersion was sampled every 30 minutes.

To 1 g each of the sampled dispersions, the liquid C prepared in accordance with Table 10 was added in an amount of 7 g in Example 11, in an amount of 5 g in Example 12, in an amount of 3 g in Example 13, or in an amount of 2 g in Example 14, and the resultant was stirred to obtain an aqueous ophthalmic composition containing the respective components in the amounts shown in Table 12.

TABLE 12

| | Aqueous ophthalmic composition | | | |
|---|---|---|---|---|
| | Example 11 | Example 12 | Example 13 | Example 14 |
| Component Concentration in liquid A (in terms of the concentration in the final aqueous composition, %) | | | | |
| Brinzolamide | 1.05 | 1.05 | 1.05 | 1.05 |
| HPMC | 0.2 | 0.2 | 0.2 | 0.2 |
| HPMCAS (AS-LF) | 0.275 | 0.275 | 0.275 | 0.275 |
| pH-adjusting agent (hydrochloric acid, sodium hydroxide) | q.s. | q.s. | q.s. | q.s. |
| Water | q.s. | q.s. | q.s. | q.s. |
| Component Concentration in liquid B (in terms of the concentration in the final aqueous composition, %) | | | | |
| Polyethylene glycol 6000 | 0.5 | 0.5 | 0.5 | 0.5 |
| Water | q.s. | q.s. | q.s. | q.s. |
| Component Concentration in liquid C (in terms of the concentration in the final aqueous composition, %) | | | | |
| Carboxyvinyl polymer (CARBOPOL 971PNF) | 0.4 | 0.4 | 0.4 | 0.4 |
| Disodium edetate | 0.01 | 0.01 | 0.01 | 0.01 |
| Sodium chloride | 0.46 | 0.46 | 0.46 | 0.46 |
| MANNITOL | 1.9 | 1.9 | 1.9 | 1.9 |
| pH-adjusting agent (hydrochloric acid, sodium hydroxide) | q.s. | q.s. | q.s. | q.s. |
| Water | q.s. | q.s. | q.s. | q.s. |
| Pre-storage absorbance | 0.418 | 0.373 | 0.44 | 0.39 |
| Evaluation (micronization) | A | A | A | A |
| 40° C. storage period (day) | 7 | 7 | 7 | 7 |
| Post-storage absorbance | 0.461 | 0.52 | 0.556 | 0.482 |
| Change in absorbance (%) | 110% | 139% | 126% | 124% |
| Change in absorbance based on a 7-day period (%) | 110% | 139% | 126% | 124% |
| Presence or absence of reversible precipitation | absent | absent | absent | absent |
| Evaluation (stability) | A | A | A | A |
| Evaluation (overall) | A | A | A | A |

Measurement of Absorbance and Time Required for Wet Grinding

The thus obtained aqueous ophthalmic compositions were each added to a glass cell having an optical path length of 10 mm, and the absorbance was measured at a wavelength of 600 nm using a spectrophotometer (NANODROP 1000, manufactured by Thermo Fisher Scientific Inc). The measurement was performed at 25° C. The time required for the absorbance to be reduced to 0.44 or less was measured as the time required for wet grinding and shown in Table 11.

As shown in Table 11, as compared to Example 11, in each of Examples 12 to 14 in which the mixture to be wet ground was diluted with the liquid C that contains the carboxyvinyl polymer, the time required for wet grinding was drastically shortened. Based on these comparisons of Example 11 and Examples 12 to 14, it is believed that, by incorporating a carboxyvinyl polymer in the mixture to be wet ground, the carboxyvinyl polymer functioned as a dispersant and the dispersion rate of brinzolamide was thereby improved.

Storage Stability

1. Change in Absorbance

The thus obtained aqueous ophthalmic compositions of Examples 11 to 14 were each stored at a temperature of 40° C. for the respective periods shown in Table 12, and the absorbance of each aqueous ophthalmic composition after the storage was measured under the same conditions as described above. The results thereof are shown in Table 12.

The post-storage absorbance and the change in absorbance, which was calculated from the pre-storage absorbance and the post-storage absorbance, are shown in Table 12. In addition, the change in absorbance based on a storage period of 7 days was calculated in the same manner as Example 1 and evaluated based on the same evaluation criteria as Example 1. The results thereof are also shown in Table 12.

2. Presence or Absence of Reversible Precipitation

The thus obtained aqueous ophthalmic compositions were each stored at a temperature of 40° C. for the respective periods shown in Table 12, and the presence or absence of precipitation of particles in each aqueous ophthalmic composition after the storage was visually observed. As a result, no precipitation after the storage was observed in these compositions. The results thereof are shown in Table 12.

From the results shown in Table 12, it is understood that the aqueous ophthalmic compositions of Examples 11 to 14 all showed favorable dispersibility and stability of the fine particles of the carbonic anhydrase inhibitor.

The disclosures of Japanese Patent Application No. 2014-143641, filed Jul. 11, 2014, and Japanese Patent Application No. 2015-048738, filed Mar. 11, 2015, are incorporated herein by reference in their entirety.

All publications, patent applications, and technical standards mentioned in this specification are herein incorporated by reference to the same extent as if each individual publication, patent application, or technical standard was specifically and individually indicated to be incorporated by reference.

What is claimed is:

1. An aqueous ophthalmic composition comprising:
   a carbonic anhydrase inhibitor;
   a cellulose derivative comprising hydroxypropylmethyl cellulose acetate succinate;
   another cellulose derivative comprising hydroxypropylmethyl cellulose; and
   water.

2. The aqueous ophthalmic composition according to claim 1, wherein a content of the carbonic anhydrase inhibitor with respect to the total mass of the aqueous ophthalmic composition is from 0.1% by mass to 10% by mass.

3. The aqueous ophthalmic composition according to claim 1, wherein a total content of the cellulose derivative with respect to the total mass of the aqueous ophthalmic composition is from 0.05% by mass to 5% by mass.

4. The aqueous ophthalmic composition according to claim 1, wherein the carbonic anhydrase inhibitor is brinzolamide.

5. The aqueous ophthalmic composition according to claim 1, wherein a content of the hydroxypropylmethyl cellulose with respect to the total mass of the aqueous ophthalmic composition is from 0.05% by mass to 5% by mass.

6. The aqueous ophthalmic composition according to claim 1, further comprising a carboxyvinyl polymer.

7. The aqueous ophthalmic composition according to claim 6, wherein a content of the carboxyvinyl polymer with respect to the total mass of the aqueous ophthalmic composition is from 0.1% by mass to 10% by mass.

* * * * *